United States Patent [19]

Georgiev et al.

[11] Patent Number: 4,777,264

[45] Date of Patent: Oct. 11, 1988

[54] 5-CARBONYL DERIVATIVES OF 3-PHENYL-3-(1H-IMADAZOL-1-YLMETHYL)-2-METHYLISOXAZOLIDINES AND RELATED COMPOUNDS THEREOF

[75] Inventors: Vassil S. Georgiev, Penfield; George B. Mullen, Avon, both of N.Y.

[73] Assignee: Pennwalt Corporation, Philadelphia, Pa.

[21] Appl. No.: 104,728

[22] Filed: Oct. 2, 1987

[51] Int. Cl.[4] ..................... A01N 43/52; C07D 233/60
[52] U.S. Cl. ...................................... 548/240; 548/341
[58] Field of Search .......................................... 548/240

[56] References Cited

U.S. PATENT DOCUMENTS

| | | | |
|---|---|---|---|
| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1975 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | Georgiev | 548/240 |
| 4,723,021 | 2/1988 | Georgiev | 548/240 |

FOREIGN PATENT DOCUMENTS

| | | | |
|---|---|---|---|
| 171137 | 2/1986 | European Pat. Off. | 548/215 |
| 54-76579 | 6/1979 | Japan . | |

OTHER PUBLICATIONS

Sokolov, S. V. et al., Chemical Abstract 55:7399 (1961) Abstractir "Isoxazole Compounds III. Synthesis of some isoxazolylazoles", Zhur. Obshchei Khim, 30, pp. 1781–1787 (1960).
Kano, H. et al., Chem. Abstract 62:9139a (1965) Abstracting French 1,376,432 (Oct. 23, 1964).
Kano, H. et al., Chemical Abstract 63:8367a (1965) Abstracting French 1,380,177 (Nov. 27, 1964).
Takahi, Y. et al., Chemical Abstract 81:22233c (1974) Abstracting Japan Kokai 7399.336 (Dec. 15, 1973).
Boyce, C. B. et al., Chemical Abstract 87:23258a (1977), Abstracting German Offen. 2,639,189 (Mar. 10, 1977).
Funaki, Y. et al., Chemical Abstract 92:128915u (1980), Abstracting Japan Kokai 79 76,579 (Jun. 19, 1979).
Kelly, R. C. et al., Chemical Abstract 93:114498u (1980), Abstracting German Offen. 2,918,878 (Nov. 22, 1979).
Haken, P. T. et al., Chemical Abstract 93:132471j (1980) Abstracting Brit. Pat. Appln. 2,024,218 (Jan. 9, 1980).

Primary Examiner—Donald G. Daus
Assistant Examiner—Mark W. Noel

[57] ABSTRACT

5-Carbonyl derivatives of 3-phenyl-3-(1-H-imidazol-1-ylmethyl)-2-methylisoxazolidines and related compounds are useful as antifungal agents.

9 Claims, No Drawings

5-CARBONYL DERIVATIVES OF 3-PHENYL-3-(1H-IMADAZOL-1-YLMETHYL)-2-METHYLISOXAZOLIDINES AND RELATED COMPOUNDS THEREOF

BACKGROUND OF THE INVENTION

This invention relates generally to substituted 2-methylisoxazolidines and more specifically to 5-carbonyl derivatives of 3-phenyl-3-(1H-imidazol-1-ylmethyl)-2-methylisoxazolidines and related compounds thereof, which are useful as antifungal agents.

BRIEF SUMMARY OF THE INVENTION

In accordance with this invention there are provided compounds of the formula:

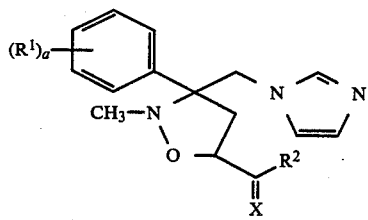

and the pharmaceutically acceptable acid addition salts thereof, in the form of their enantiomers or mixtures of their enantiomers including diastereomeric pairs of such enantiomers,
wherein;
a=1 or 2,
X is selected from oxygen and hydroxyimino,
$R^1$ is selected from hydrogen, halogen, lower alkyl, lower alkoxy and combinations thereof, and
$R^2$ is selected from lower alkyl, lower alkoxy, substituted phenoxy and substituted phenylamino groups, wherein the phenyl substituents are selected from lower alkyl, halogen and lower alkoxy groups.

DETAILED DESCRIPTION OF THE INVENTION

The compounds of this invention are useful as antifungal agents. They have in vitro activity against yeast and systemic mycoses and dermatophytes as determined by broth and agar testing techniques [McGinnis, M. R., *Laboratory Handbook of Medical Mycology*, Academic Press, New York, N.Y. (1980)]. The compounds prepared in Examples 1 and 5 were found to have good to moderate inhibitory activity against a broad spectrum of organisms including *Trichophyton mentagrophytes, Trichophyton rubrum, Trichophyton tonsurans, Epidermophyton floccosum* and *Candida stellatoidea*. For example, the compound of Example 5 was active against *Trichophyton sp., Epidermophyton floccosum, Microsporum canis*, and *Candida stellatoidea* at minimum inhibitory concentrations, MIC, ranging between 0.2 to 7 μg/ml.

Because of their antifungal activity, the compounds of this invention can be used, for example, in suitable liquid, semisolid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

In addition to its antifungal activity, the compound of Example 1 also exhibited oral antiulcer activity and in vitro platelet aggregation-inhibiting activity.

The compounds of this invention are those of the formula:

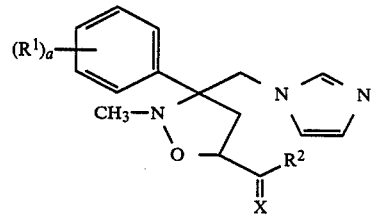

and the pharmaceutically acceptable acid addition salts thereof, in the form of their enantiomers or mixtures of their enantiomers including diastereomeric pairs of such enantiomers,
wherein;
a=1 or 2,
X is selected from oxygen and hydroxyimino,
$R^1$ is selected from hydrogen, halogen, lower alkyl and lower alkoxy and combinations thereof, and
$R^2$ is selected from lower alkyl, lower alkoxy, substituted phenoxy and substituted phenylamino groups, wherein the phenyl rings can be substituted with lower alkyl, halogen and lower alkoxy groups.

By halogen is meant chlorine, bromine, fluorine and iodine with chlorine and fluorine being preferred. By lower alkyl is meant alkyl groups containing one to four (1-4) carbons and by lower alkoxy is meant alkoxy groups containing one to six (1-6) carbons. In either case groups with three or more carbons can have a branched or unbranched chain.

The 5-carbonyl derivatives of 3-phenyl-3-(1H-imidazol-1-ylmethyl)-2-methylisoxazolidines of the invention are obtained as a mixture of cis- and trans-diastereomers due to the presence of two asymmetric carbon atoms in the isoxazolidine ring. The diastereomeric mixture is conveniently separated by flash chromatography on silica gel using halogenated hydrocarbons (preferably dichloromethane and chloroform), alkanols (preferably methanol and ethanol). ethyl acetate and such, as eluents. The eluents may be used alone or in combinations, such as the ones comprised of 95-99% halogenated hydrocarbon and 1-5% alkanol by volume. The stereochemistry of the two asymmetric carbon atoms in the isoxazolidine ring may be determined by conventional methods that include x-ray crystallography, nuclear magnetic resonance spectroscopy, circular dichroism and optical rotatory dispersion. Both the cis- and trans-diastereomers are resolvable into their optical enantiomers with (+)- and (−)-optical rotations by standard techniques such as fractional recrystallization of the diastereomeric salts with optically active organic acids such as (+)- and (−)-tartaric acid, (+)- and (−)-dibenzoyltartaric acid and the like.

The compounds of the invention can be prepared as illustrated in the following diagram. The synthesis of the nitrone precursors 1 is accomplished by reacting an appropriately substituted 2-imidazolylacetophenone with N-methylhydroxylamine hydrochloride as described in our copending application Ser. No. 900,856 filed Aug. 27, 1985 whose disclosure is incorporated herein by reference. Subsequent reaction of the nitrone with an appropriate 1-alkene derivative 2 provides a diastereomeric mixture of the desired cis- and trans-5-carbonyl derivatives of the 3-phenyl-3-(1H-imidazol-1-ylmethyl)-2-methylisoxazolidines 3. Further reaction of the ketone compounds such as 3' with hydroxylamine hydrochloride and sodium hydroxide provides the oximes 4.

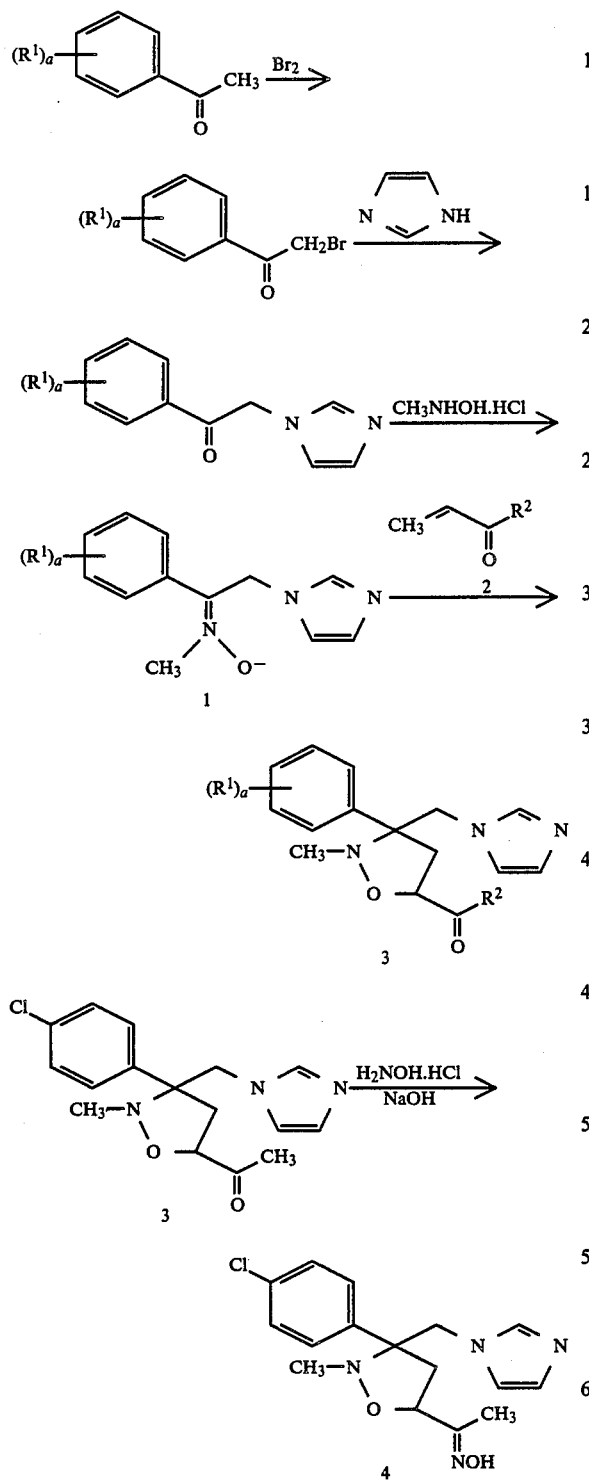

The compounds of the invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation the compounds of the invention is further illustrated by the following examples.

PREPARATION OF PRECURSORS 4-methylphenyl acrylate, 4-chlorophenyl acrylate and N-4-chlorophenyl acrylamide can be prepared from commercially available acryloyl chloride by using standard literature procedures. For example, reaction of 4-chloroaniline with 1 equivalent of acrylol chloride in tetrahydrofuran containing 1 equivalent of triethylamine gave (N-(4-chlorophenyl)acrylamide.

EXAMPLE 1

Ethyl 3-(4-Chlorophenyl)-3-(1H-imidazol-1-ylmethyl)-2-methylisoxazolidine-5-carboxylate (3, $R^1$=4-Cl, $R^2$=OEt)

A solution of 22.47 g (0.090 mol) of 1-(4-chlorophenyl)-2-(1H-imidazol-1-yl)-N-methylethanimine N-oxide (1, $R^1$=4-Cl) [which can be prepared by reacting 2-(1H-imidazol-1-yl)-4'-chloroacetophenone (38.77 g, 0.176 mol), N-methylhydroxylamine hydrochloride (17.63 g, 0.211 mol) and sodium acetate (34.6 g, 0.422 mol in 470 ml ethanol] and 20 ml (0.18 mol) of ethyl acrylate (2, $R^2$=OEt) in 150 ml of toluene is refluxed for 45 hours under a nitrogen atmosphere, cooled to ambient temperature and concentrated in vacuo. The residual dark oil, containing a cis- and trans-diastereomeric mixture of compound 3 ($R^1$=4-Cl, $R^2$=OEt) is flash-chromatographed on neutral silica gel using ethyl acetate as eluent.

Isomer A (1.94 g, 6.2%) has a melting point of 150°–152° C. (ethyl acetate). Anal. Calcd. for $C_{17}H_{20}ClN_3O_3$: C, 58.37; H, 5.76; Cl, 10.13; N, 12.01. Found: C, 58.39; H, 5.93; Cl, 10.11; N, 12.03.

EXAMPLE 2

4-Methylphenyl 3-(1H-Imidazol-1-ylmethyl)-2-methyl-3-phenylisoxazolidine-5-carboxylate (3, $R^1$=H, $R^2$=OC$_6$H$_4$CH$_3$-4)

A solution of 7.60 g (0.043 mol) of 2-(1H-imidazol-1-yl)-N-methyl-1-phenylethanimine N-oxide (1, $R^1$=H) and 10.55 g (0.065 mol) of 4-methylphenyl acrylate (2, $R^2$=OC$_6$H$_4$CH$_3$-4) in 200 ml of toluene is heated to 55°–60° C. and stirred for 18 hours under a nitrogen atmosphere, then cooled to ambient temperature and concentrated in vacuo, leaving a dark viscous oil containing a cis- and trans-diastereomeric mixture of compound 3 ($R^1$=H, $R^2$=OC$_6$H$_4$CH$_3$-4). Isomer A is obtained by crystallization from ethyl ether; yield: 3.80 g (23%).

Isomer A has a melting point of 149°–151° C. (ethyl acetate). Anal. Calcd. for $C_{22}H_{23}N_3O_3$: C, 70.01; H, 6.14; N, 11.13. Found: C, 69.98; H, 6.24; N, 11.17.

EXAMPLE 3

4-Chlorophenyl 3-(4-Fluorophenyl)-3-(1H-imidazol-1-ylmethyl)-2-methylisoxazolidine-5-carboxylate (3, $R^1$=4-F, $R^2$=OC$_6$H$_4$Cl-4)

Compound 3 ($R^1$=4-F, $R^2$=OC$_6$H$_4$Cl-4) is prepared by a method similar to that described in Example 2 from 1-(4-fluorophenyl)-2-(1H-imidazol-1-yl)-N-methylethanimine N-oxide (1, $R^1$=4-F) and 4-chlorophenyl acrylate (2, $R^2$=OC$_6$H$_4$Cl-4). The resulting cis- and trans-diastereomeric mixture of compound 3 ($R^1$=4-F, $R^2$=OC$_6$H$_4$Cl-4) is flash-chromatographed on neutral silica gel using ethyl acetate as eluent. Isomer A has a melting point of 146°–148° C. (ethyl ether).

EXAMPLE 4

4-Chlorophenyl-3-(4-Chlorophenyl)-3-(1H-imidazol-1-ylmethyl)-2-methylisoxazolidine-5-carboxylate (3, $R^1$=4-Cl, $R^2$=OC$_6$H$_4$Cl-4)

Compound 3 ($R^1$=4-Cl, $R^2$=OC$_6$H$_4$Cl-4) is prepared by a method similar to that described in Example 2 from 1-(4-chlorophenyl)-2-(1H-imidazol-1-yl)-N-methylethanimine N-oxide (1, $R^1$=4-Cl) and 4-chlorophenyl acrylate (2, $R^2$=OC$_6$H$_4$Cl-4). The resulting cis- and trans-diastereomeric mixture of compound 3 ($R^1$=4-Cl, $R^2$=OC$_6$H$_4$Cl-4) is flash-chromatographed on neutral silica gel using ethyl acetate as eluent.

Isomer A has a melting point of 141°–144° C. (ethyl acetate).

EXAMPLE 5

N-(4-Chlorophenyl) 3-(4-Chlorophenyl)-3-(1H-imidazol-1-ylmethyl)-2-methylisoxazolidine-5-carboxamide (3, $R^1$=4-Cl, $R^2$=NHC$_6$H$_4$Cl-4)

A solution of 34.1 g (0.14 mol) of 1-(4-chlorophenyl)-2-(1H-imidazol-1-yl)-N-methylethanimine N-oxide (1, $R^1$=4-Cl) and 34.4 g (0.19 mol) of N-(4-chlorophenyl)acrylamide (2, $R^2$=NHC$_6$H$_4$Cl-4) in 300 ml of toluene is refluxed for 18 hours under a nitrogen atmosphere, cooled to ambient temperature and concentrated in vacuo. The residual dark oil, containing a cis- and trans-distereomeric mixture of compound 3 ($R^1$=4-Cl, $R^2$=NHC$_6$H$_4$Cl-4), is flash-chromatographed on neutral silica gel using a 99:1 by volume mixture of chloroform and methanol as eluent.

Isomer A (12.73 g, 21%) has a melting point of 197°–198° C. (ethyl acetate). Anal. Calcd. for $C_{21}H_{20}Cl_2N_4O_2$: C, 58.48; H, 4.67; Cl, 16.44; N, 12.99. Found: C, 58.67; H, 4.82; Cl, 16.21; N, 13.01.

Isomer B (5.72 g, 9.5%) has a melting point of 204°–205° C. (ethyl acetate). Anal. Calcd. for $C_{21}H_{20}Cl_2N_4O_2$: C, 58.48; H, 4.67; Cl, 16.44; N, 12.99. Found: C, 58.53; H, 4.76; Cl, 16.34; N, 13.03.

EXAMPLE 6

1-[3-(4-Chlorophenyl)-3-(1H-imidazol-1-ylmethyl)-2-methyl-isoxazolidin-5-yl]ethanone (3, $R^1$=4-Cl, $R^2$=CH$_3$)

A solution of 16.20 g (0.0649 mol) of 1-(4-chlorophenyl)-2-(1H-imidazol-1-yl)-N-methylethanimine N-oxide (1, $R^1$=4-Cl) and 6.42 ml (0.0791 mol) of methyl vinyl ketone (2, $R^2$=CH$_3$) in 450 ml of toluene is heated to reflux for 4 hours under a nitrogen atmosphere, cooled to ambient temperature and concentrated in vacuo. The residual dark oil, containing a cis- and trans-diastereomeric mixture of compound 3 ($R^1$=4-Cl, $R^2$=CH$_3$) is flash-chromatographed on neutral silica gel using a 98:2 by volume mixture of chloroform and methanol as eluent.

Isomer A (12.27 g, 59%) has a melting point of 147°–149° C. (ethyl acetate). Anal. Calcd. for $C_{16}H_{18}ClN_3O_2$: C, 60.09; H, 5.67; Cl, 11.09; N, 13.14. Found: C, 60.14; H, 5.85; Cl, 11.26; N, 13.17.

EXAMPLE 7

1-[3-(4-Chlorophenyl)-3-(1H-imidazol-1-ylmethyl)-2-methylisoxazolidin-5-yl]ethanone oxime (4)

Under a nitrogen atmosphere, a solution of 3.00 g (0.00938 mol) of 1-[3-(4-chlorophenyl)-3-(1H-imidazol-1-ylmethyl)-2-methylisoxazolidin-5-yl]ethanone [isomer A (3, $R^1$=4-Cl, $R^2$=CH$_3$)], 0.69 g (0.010 mol) of hydroxylamine hydrochloride and 0.60 g (0.015 mol) of sodium hydroxide in 75 ml of ethanol is refluxed for 1 hour, cooled to ambient temperature, neutralized with 0.1N hydrochloric acid, and extracted with chloroform (2×50 ml). The combined organic extract is washed with 50 ml of saturated aqueous sodium chloride, dried over anhydrous magnesium sulfate and concentrated in vacuo to give a white solid. Crystallization from ethanol gives 1.57 g (50%) of compound 4, melting point 214°–216° C. (ethanol). Anal. Calcd. for $C_{16}H_{19}ClN_4O_2$: C, 57.40; H, 5.72; Cl, 10.59; N, 16.73. Found: C, 57.24; H, 5.80; Cl, 10.70; N, 16.62.

EXAMPLE 8

3-(1H-Imidazol-1-ylmethyl)-2-methyl-3-(substituted phenyl)-5-carboxylic acid 4-methoxyphenyl esters By following the method of Example 2 and substituting 4-methoxyphenyl acrylate for 4-methylphenyl acrylate, and substituting for 2-(1H-imidazol-1-yl)-N-methyl-1-phenylethanimine N-oxide one of the following compounds;

1(4-methoxyphenyl)-2-(1H-imidazol-1-yl)-N-methylethanimine N-oxide, 1-(4-methylphenyl)-2-(1H-imidazol-1-yl)-N-methylethanimine N-oxide, 1-(4-chloro-3-methylphenyl)-2-(1H-imidazol-1-yl)-N-methylethanimine N-oxide, 1-(3,4-dichlorophenyl)-2-(1H-imidazol-1-yl)-N-methylethanimine N-oxide, 1-(3-methoxyphenyl)-2-(1H-imidazol-1-yl)-N-methylethanimine N-oxide, or 1-(3-methylphenyl)-2-(1H-imidazol-1-yl)-N-methylethanimine, the corresponding 3-(1H-imidazol-1-ylmethyl)-2-methyl-3-(substituted phenyl)-5-carboxylic acid 4-methoxyphenyl esters can be prepared.

Salts of the compounds of the invention can be prepared as known in the art, for example, by dissolving the compound in a 10:1 by volume mixture of ethanol and aqueous acid such as HCl or HNO$_3$, evaporating the solvent, and then recrystallizing the crude salt, for example, from methanol-ether, 1:3 by volume in the case of HCl salts, and ethanol in the case of HNO$_3$ salts.

We claim:
1. A compound of the formula:

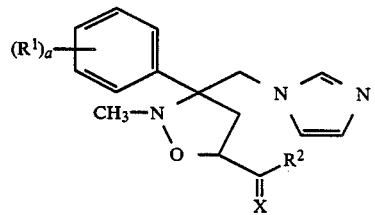

a=1 or 2,

X is selected from oxygen and hydroxyimino, $R^1$ is selected from hydrogen, halogen, lower alkyl, lower alkoxy and combinations thereof, provided that the ortho position is hydrogen and $R^2$ is selected from lower alkyl, lower alkoxy, substituted phenoxy and substituted phenylamino groups, wherein the phenyl substituents are selected from one to three of lower alkyl, halogen and lower alkoxy groups.

2. The compound of claim 1 wherein the compound is ethyl 3-(4-chlorophenyl)-3-(1H-imidazol-1-ylmethyl)-2-methylisoxazolidine-5-carboxylate.

3. The compound of claim 1 wherein the compound is 4-methylphenyl 3-(1H-imidazol-1-ylmethyl)-2-methyl-3-phenylisoxazolidine-5-carboxylate.

4. The compound of claim 1 wherein the compound is 4-chlorophenyl 3-(4-fluorophenyl)-3-(1H-imidazol-1-ylmethyl)-2-methylisoxazolidine-5-carboxylate.

5. The compound of claim 1 wherein the compound is 4-chlorophenyl 3-(4-chlorophenyl)-3-(1H-imidazol-1-ylmethyl)-2-methylisoxazolidine-5-carboxylate.

6. The compound of claim 1 wherein the compound is N-(4-chlorophenyl) 3-(4-chlorophenyl)-3-(1H-imidazol-1-ylmethyl)-2-methylisoxazolidine-5-carboxamide.

7. The compound of claim 1 wherein the compound is 1-[3-(4-chlorophenyl)-3-(1H-imidazol-1-ylmethyl)-2-methylisoxazolidine-5-yl]ethanone.

8. The compound of claim 1 wherein X is hydroxyimino.

9. The compound of claim 8 wherein the compound is 1-[3-(4-chlorophenyl)-3-(1H-imidazol-1-ylmethyl)-2-methylisoxazolidine-5-yl]ethanone oxime.

* * * * *